(12) United States Patent
Kimura-Ohba et al.

(10) Patent No.: US 10,827,946 B2
(45) Date of Patent: Nov. 10, 2020

(54) FRACTIONAL ANISOTROPY IN MRI AS AN INDICATOR OF REVERSIBLE PATHOLOGY

(71) Applicant: STC.UNM, Albuquerque, NM (US)

(72) Inventors: Shihoko Kimura-Ohba, Osaka (JP); Laurel Sillerud, Albuquerque, NM (US)

(73) Assignee: UNM Rainforest Innovations, Albuquerque, NM (US)

( * ) Notice: Subject to any disclaimer, the term of this patent is extended or adjusted under 35 U.S.C. 154(b) by 381 days.

(21) Appl. No.: 15/756,221

(22) PCT Filed: Aug. 31, 2016

(86) PCT No.: PCT/US2016/049720
§ 371 (c)(1),
(2) Date: Feb. 28, 2018

(87) PCT Pub. No.: WO2017/040678
PCT Pub. Date: Mar. 9, 2017

(65) Prior Publication Data
US 2018/0249926 A1    Sep. 6, 2018

Related U.S. Application Data

(60) Provisional application No. 62/212,458, filed on Aug. 31, 2015.

(51) Int. Cl.
*A61B 5/055*   (2006.01)
*A61B 6/03*    (2006.01)
(Continued)

(52) U.S. Cl.
CPC ............ *A61B 5/055* (2013.01); *A61B 5/4094* (2013.01); *A61B 5/4842* (2013.01);
(Continued)

(58) Field of Classification Search
CPC ............ A61B 2503/40; A61B 2503/42; A61B 2576/026; A61B 5/055; A61B 5/4094;
(Continued)

(56) References Cited

U.S. PATENT DOCUMENTS

2011/0282183 A1   11/2011  Song et al.
2012/0046538 A1   2/2012   Raghavan et al.
2012/0280686 A1*  11/2012  White ............... G01R 33/56341
                                                    324/309

OTHER PUBLICATIONS

Federal Institute of Industrial Property; International Search Report & Written Opinion for PCT/US2016/049720; dated Aug. 12, 2016; 7 pages; Moscow; RU.
(Continued)

*Primary Examiner* — Mark D Remaly
(74) *Attorney, Agent, or Firm* — Keith Vogt, Ltd.; Keith A. Vogt

(57) ABSTRACT

The present invention concerns a method for determining whether brain regions of interest having reversible or irreversible pathology. The method includes acquiring over a predetermined period of time a plurality of magnetic resonance imaging (MRI) images for each brain region of interest; analyzing the MRI images to obtain quantitative measurements of the fractional anisotropy (FA) for each brain region of interest and determining that brain regions of interest have reversible pathology when the measured FA increases and then decreases over the predetermined period of time.

23 Claims, 13 Drawing Sheets

(51) Int. Cl.
*G06T 7/48* (2017.01)
*A61B 5/00* (2006.01)
*G06T 7/00* (2017.01)
*G01R 33/563* (2006.01)

(52) U.S. Cl.
CPC .............. *A61B 5/4878* (2013.01); *A61B 6/03* (2013.01); *G06T 7/0012* (2013.01); *G06T 7/48* (2017.01); *A61B 2503/40* (2013.01); *A61B 2503/42* (2013.01); *A61B 2576/026* (2013.01); *G01R 33/56341* (2013.01); *G06T 2207/10092* (2013.01); *G06T 2207/30016* (2013.01)

(58) Field of Classification Search
CPC ....... A61B 5/4842; A61B 5/4878; A61B 6/03; G01R 33/56341; G06T 2207/10092; G06T 2207/30016; G06T 7/0012; G06T 7/48
See application file for complete search history.

(56) References Cited

OTHER PUBLICATIONS

Belder et al; Diffusion Tensor Imaging Provides and Insight into the Microstructure of Meningiomas, High-Grade Gliomas, and Peritumoral Edema; J. Comput Assist Tomogr., 2012, vol. 36, No. 5; pp. 577-582.

Balasubramanian et al; Correlation of Fractional anisotropy (FA) changes in demyelination lesion with its surrounding edema in an experimental model; Proc. Intl. Soc. Mag. Reason. Med 18, 2010; p. 4513.

* cited by examiner

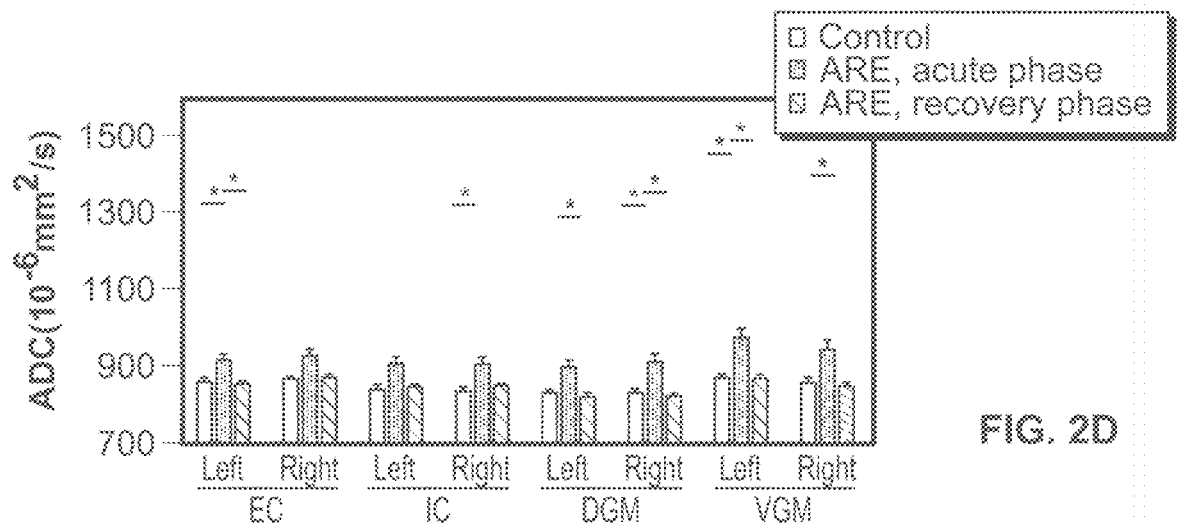
FIG. 2D
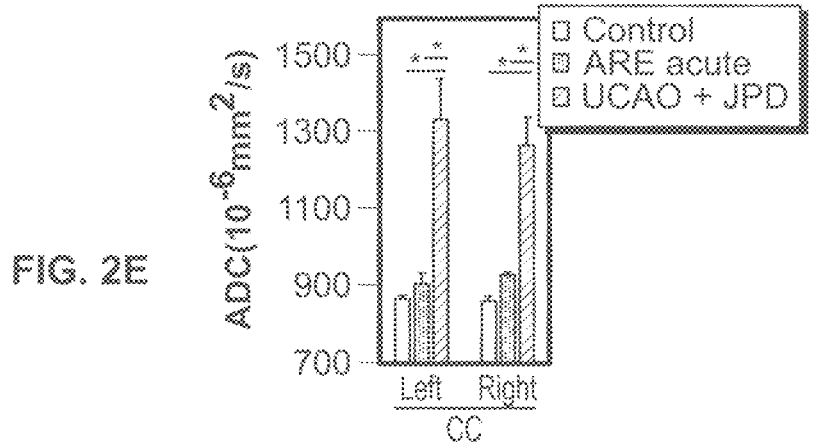
FIG. 2E
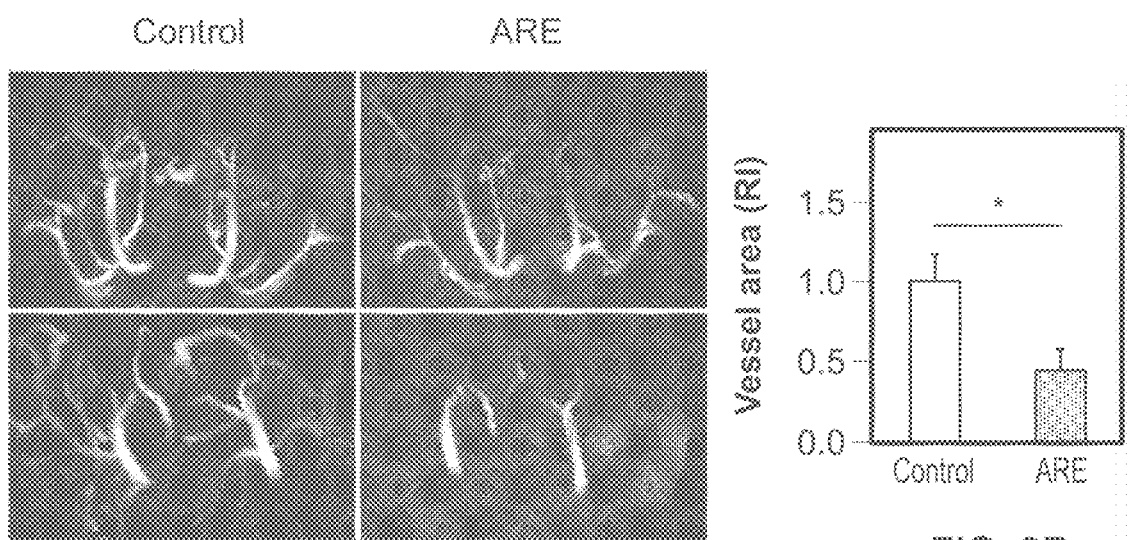
FIG. 3A
FIG. 3B

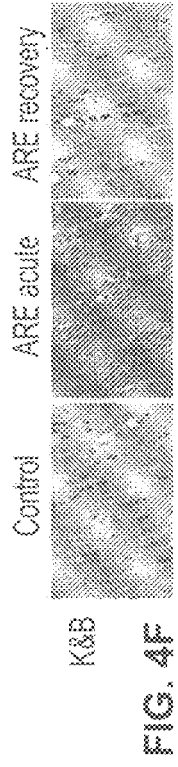
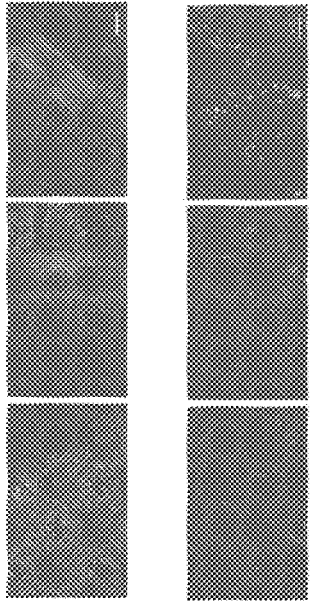
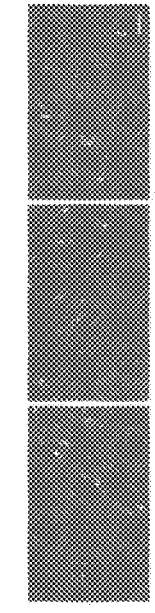
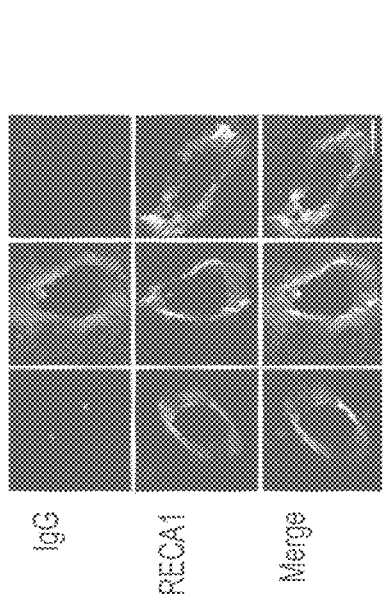
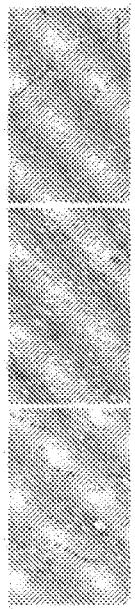
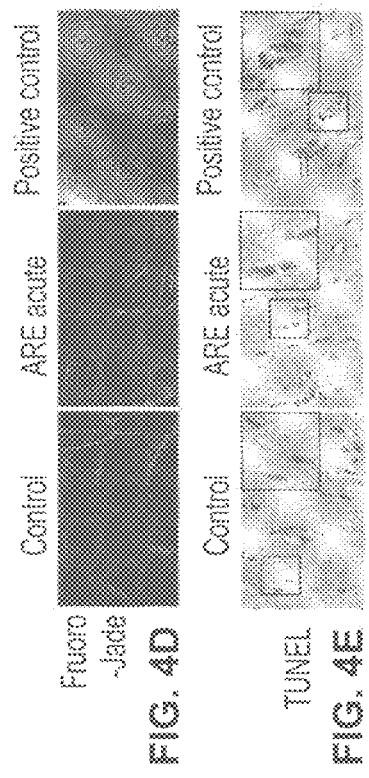

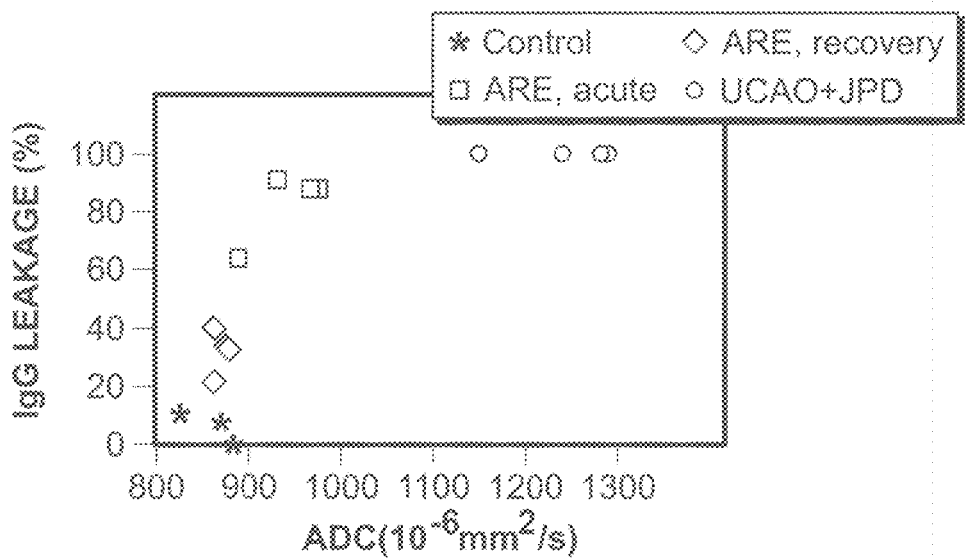
FIG. 5A
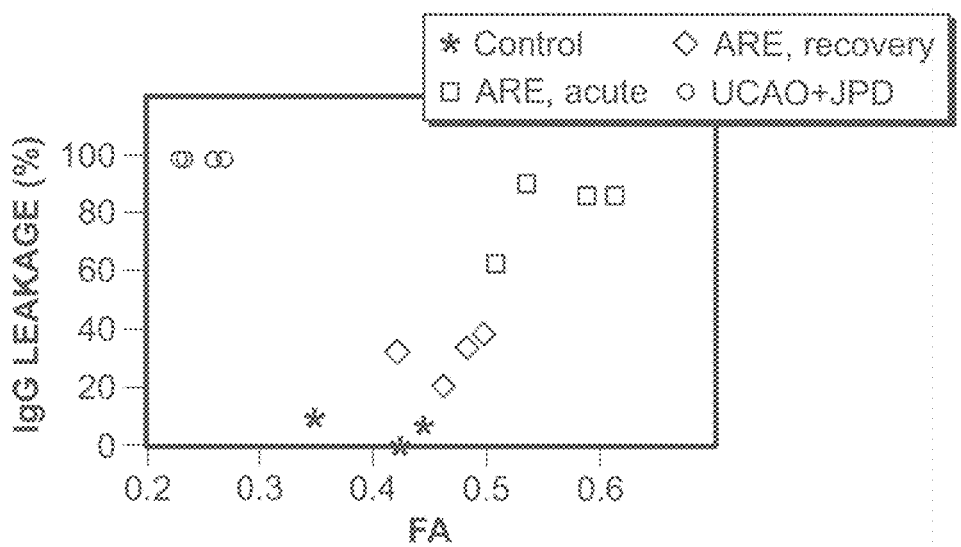
FIG. 5B
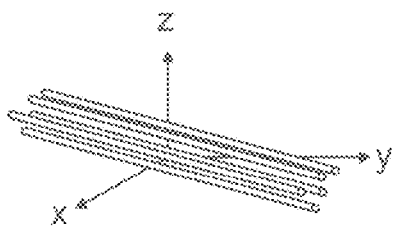 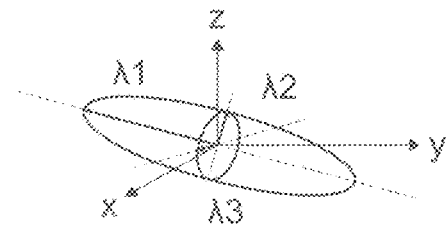
Axial diffusivity (AD) = $\lambda_1$
Radial diffusivity (RD) = $\dfrac{\lambda_2 + \lambda_3}{2}$
Mean diffusivity (MD) = $\dfrac{\lambda_1 + \lambda_2 + \lambda_3}{3}$
$$FA = \sqrt{\dfrac{(\lambda_1 - MD)^2 + (\lambda_2 - MD)^2 + (\lambda_3 - MD)^2}{2(\lambda_1^2 + \lambda_2^2 + \lambda_3^2)}}$$
FIG. 6A Table 3. Summary of MRI Fractional Apparent Diffusion Coefficient Changes In ARE and VCI.

|  | LCC | RCC |
|---|---|---|
| Control | 0.000869 | 0.000872 |
| ARE; Acute | 0.000902 | 0.000926 |
| VCI model | 0.001148 | 0.001103 |
| SE control | 9.34E-06 | 8.42E-06 |
| SE Acute | 1.56E-05 | 1.68E-05 |
| SE VCI moc | 0.000134 | 0.000113 |

Table 4. Summary of Fractional Anisotropy Changes in ARE during Acute and Recovery Phases.

|  | LEC | REC | LIC | RIC | LDGM | RDGM | LVGM | RVGM |
|---|---|---|---|---|---|---|---|---|
| Control | 0.409125 | 0.43075 | 0.55 | 0.561375 | 0.201875 | 0.22025 | 0.232125 | 0.25725 |
| ARE; Acute | 0.464235 | 0.479765 | 0.658118 | 0.636 | 0.304588 | 0.327118 | 0.355706 | 0.367647 |
| ARE; Recovery | 0.40725 | 0.418125 | 0.571625 | 0.555625 | 0.194625 | 0.209 | 0.24 | 0.247625 |
| SE control | 0.014267 | 0.007326 | 0.013735 | 0.009146 | 0.007729 | 0.005394 | 0.009278 | 0.01575 |
| SE Acute | 0.012735 | 0.011463 | 0.017866 | 0.014517 | 0.020142 | 0.023546 | 0.026968 | 0.021308 |
| SE Recovery | 0.009604 | 0.010826 | 0.016286 | 0.008615 | 0.008033 | 0.004075 | 0.007538 | 0.007221 |

Table 5. Fractional Anisotropy Changes In ARE during the Acute Phase and Irreversible Vascular Occlusion Model.

|  | LCC | RCC |
|---|---|---|
| Control | 0.45875 | 0.4695 |
| ARE; Acute | 0.543058824 | 0.563764706 |
| VCI model | 0.295166667 | 0.333666667 |
| SE control | 0.020489326 | 0.023328401 |
| SE Acute | 0.012270382 | 0.014942667 |
| SE VCI model | 0.033496683 | 0.032353945 |

FRACTIONAL ANISOTROPY IN MRI AS AN INDICATOR OF REVERSIBLE PATHOLOGY

RELATED APPLICATIONS

This application claims the benefit of U.S. Provisional Application No. 62/212,458 filed Aug. 31, 2015 and herein incorporated by reference.

BACKGROUND OF THE INVENTION

Brain vasogenic edema, involving disruption of the blood-brain barrier, is a common pathological condition in several neurological diseases, with a heterogeneous prognosis. It is sometimes reversible, as in posterior reversible encephalopathy syndrome, but often irreversible and current clinical tools are insufficient to reveal its reversibility.

Brain edema, a fundamental and universal pathological condition of neurological diseases, is typically classified into two types; vasogenic and cytotoxic. Brain vasogenic edema results after the disruption of the blood-brain barrier (BBB), whereas cytotoxic edema is caused by cellular swelling of neurons or astrocytes due to abnormal fluxes of sodium and other ions. The lesions where the two types of edema coexist are likely to develop permanent damage.

Whether or not the vasogenic edema is reversible strongly modulates the prognosis for patients. When vasogenic edema occurs in multiple sclerosis and small vessel disease, the edema is irreversible and the prognosis is mainly unfavorable. On the other hand, in the Posterior Reversible Encephalopathy Syndrome (PRES), the prognosis is usually favorable. PRES is unique in that it is one of a few diseases which present with only vasogenic edema and whose clinical course is usually reversible. The over-dose usage of certain drugs, such as cyclosporine A (CsA) in the presence of hypertension, is a risk factor for the occurrence of PRES; endothelial injury, vasoconstriction, and increasing vascular permeability induced by CsA predisposes patients at risk to PRES.

Although the prognosis of vasogenic edema is heterogeneous as described above, its reversibility cannot be predicted using current clinical tools. For example, increases in the apparent diffusion coefficient (ADC) of water in magnetic resonance (MR) images are used to diagnose vasogenic edema, but do not predict the prognosis. Diffusion tensor imaging (DTI) is frequently used to analyze changes at the cellular and microstructural level. The Fractional Anisotropy (FA) is a DTI parameter, which represents the anisotropy of water diffusion in the brain. It is generally accepted that an FA decrease indicates demyelination and/or axonal injury in white matter, and is associated with a poor prognosis. On the other hand, an FA increase has been reported to reflect axonal regeneration, plasticity or gliosis.

BRIEF SUMMARY OF THE INVENTION

In one embodiment, the present invention establishes that increased fractional anisotropy (FA) in magnetic resonance imaging is associated with the reversibility of vasogenic edema. As a result, the present invention has prognostic capability by measuring the FA during and after vasogenic edema.

The present invention establishes that an FA increase is observed during vasogenic edema. By establishing a model for reversible vasogenic edema, it has been found that vasogenic edema induces an FA increase only when myelin structures are conserved. As a result, an FA increase during vasogenic edema was found to be a marker for potential recovery, whereas an FA decrease was associated with chronic brain injury.

In another embodiment, the present invention provides a method for determining whether brain regions of interest having reversible or irreversible pathology comprising the steps of: acquiring over a predetermined period of time a plurality of magnetic resonance imaging (MRI) images for each brain region of interest; analyzing the MRI images to obtain quantitative measurements of the fractional anisotropy (FA) for each brain region of interest over the predetermined period of time; and determining that brain regions of interest have reversible pathology when the measured FA increases and then decreases over the predetermined period of time. In other embodiments, the amount of decrease is to a level which is at the first measured level, or a normal level or an original level. Pathologies that may be evaluated include, but are not limited to, vasogenic edema, cytotoxic edema, chronic traumatic encephalopathy, and acute reversible encephalopathy (ARE).

In other embodiments, the present invention provides methods wherein FA increases by 10 to 50 percent in white and gray matter and returns to original levels; wherein FA is measured to indicate the acute phase of reversible vasogenic brain edema; wherein FA is measured to determine damage to both white and gray tracts of the brain; wherein FA is measured to determine damage to white tracts of the brain; wherein FA is measured to determine damage to gray tracts of the brain; wherein FA is measured to examine brain lesions; wherein FA is measured to determine IgG leakage; wherein FA is to determine leakage from blood vessels of plasma components that accumulate between the myelin sheaths and compress the myelinated axons; wherein FA is measured by MR-DTI to detect reversible vasogenic edema; wherein FA is measured to locate areas of the brain intervention as well as a methodology that measures FA increase as a marker for reversibility and conserved myelination.

In other embodiments, the present invention provides a method for determining for a mammalian subject that has suffered vasogenic edema whether the subject has brain regions of interest having reversible or irreversible vasogenic edema comprising the steps of, acquiring over a predetermined period of time 1) a plurality of magnetic resonance imaging (MRI) images for each brain region of interest; analyzing the MRI images to obtain quantitative measurements of the fractional anisotropy (FA) for each brain region of interest over the predetermined period of time; 2) acquiring a plurality of T2 weighted images over said predetermined period of time for each brain region of interest, analyzing said T2 weighted images to obtain quantitative measurements of the intensity of each image for each brain region of interest over the predetermined period of time; 3) acquiring a plurality of apparent diffusion coefficient values over said predetermined period of time for each brain region of interest, analyzing the apparent diffusion coefficient values to obtain quantitative measurements of the diffusion coefficient value for each brain region of interest over the predetermined period of time; 4) acquiring a plurality of radial diffusivity values over the predetermined period of time for each brain region of interest, analyzing the radial diffusivity values to obtain quantitative measurements of the radial diffusivity value for each brain region of interest over the predetermined period of time; and 5) determining that brain regions of interest have reversible vasogenic edema when the measured FA, said T2 weighted image intensity and said diffusion coefficient values increase and then decreases over the predetermined period of time and said measured radial diffusivity values remain the same or decrease over the predetermined period of time. The decrease may be to a first measured level, an original level or a normal level.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

In the drawings, which are not necessarily drawn to scale, like numerals may describe substantially similar components throughout the several views. Like numerals having different letter suffixes may represent different instances of substantially similar components. The drawings illustrate generally, by way of example, but not by way of limitation, a detailed description of certain embodiments discussed in the present document.

FIG. 1. Establishment of a rodent acute reversible encephalopathy (ARE) model.

FIG. 2. Brains of ARE model show a reversible increase of FA. (FIGS. 2B, 2C, 2D and 2E) FA (FIG. 2B and FIG. 2C) and ADC (FIG. 2D and FIG. 2E) values in white matter and gray matter of acute- and recovery-phase ARE, unilateral carotid arterial occlusion on JPD (UCAO-JPD), and control. Because main lesions of UCAO-JPD were restricted to the corpus callosum, the comparison between acute ARE, UCAO-JPD, and control were separately shown in FIG. 2C and FIG. 2E. EC, external capsule. Data, means±SE, n=4 to 16, *P<0.05.

FIG. 3. MRA of ARE acute animals revealed vasoconstriction and narrowing of distal branch arteries. (FIG. 3A) 3D MRA image of acute-phase ARE and its control. (FIG. 3B) Relative area of vascular beds in acute-phase ARE and its control. RI, relative index. Data, means±SE, n=4, *P<0.05.

FIG. 4. Brain lesions of ARE model revealed IgG leakage without apparent demyelination. (FIG. 4A) IgG leakage seen in ARE model. Upper panels, lower magnification views of left corpus callosum and visual cortex from acute- and recovery-phase ARE and control animals. Leaked IgG was taken up by oligodendrocytes and astrocytes in acute ARE. (FIG. 4B) Higher magnification views of IgG leakage in left corpus callosum. IgG leaked outside the vessel in acute ARE (Middle column). RECA-1, a marker of endothelial cells; DAPI was used for nuclei. (FIG. 4C and FIG. 4D) Fluoro-Jade (FIGS. 4F & FIG. 4J) staining of left cortex (FIG. 4C) and TUNEL staining of corpus callosum (FIG. 4D), of acute-phase ARE and control. Rat brain sections subjected to MCAO were used as positive controls for FIGS. 4F & FIG. 4J and nuclease-treated brains for TUNEL. (FIG. 4E) Model of reversible IgG leakage by the stimulated by CsA injections. Scale bars indicate (FIG. 4A, FIG. 4B, FIGS. 4D and 4G, 4H & 4I) 20 μm, and (FIG. 4C) 400 μm.

FIG. 5. Relationship between histological and diffusion MR data for vasogenic edema in matched brain slices. Scatter plots of IgG leakage area and either (FIG. 5A) ADC or (FIG. 5B) FA values in left corpus callosum of acute- and recovery-phase ARE, UCAO-JPD, and control.

FIG. 6. Increased axial, but not radial, diffusivity due to IgG leakage is the cause of FA increase in acute ARE. (FIG. 6A) Schematic representation of MRI parameters. Left; axonal direction of the real world. Right; diffusion tensor. $\lambda_1$, $\lambda_2$, $\lambda_3$; eigenvalues calculated by diagonalization. Of note, $\lambda_1$ is the major eigenvalue and its corresponding eigenvector is assumed to be parallel to the axonal orientation. Equations for AD, RD, MD and FA are shown.

DETAILED DESCRIPTION OF THE INVENTION

Figure 1A:
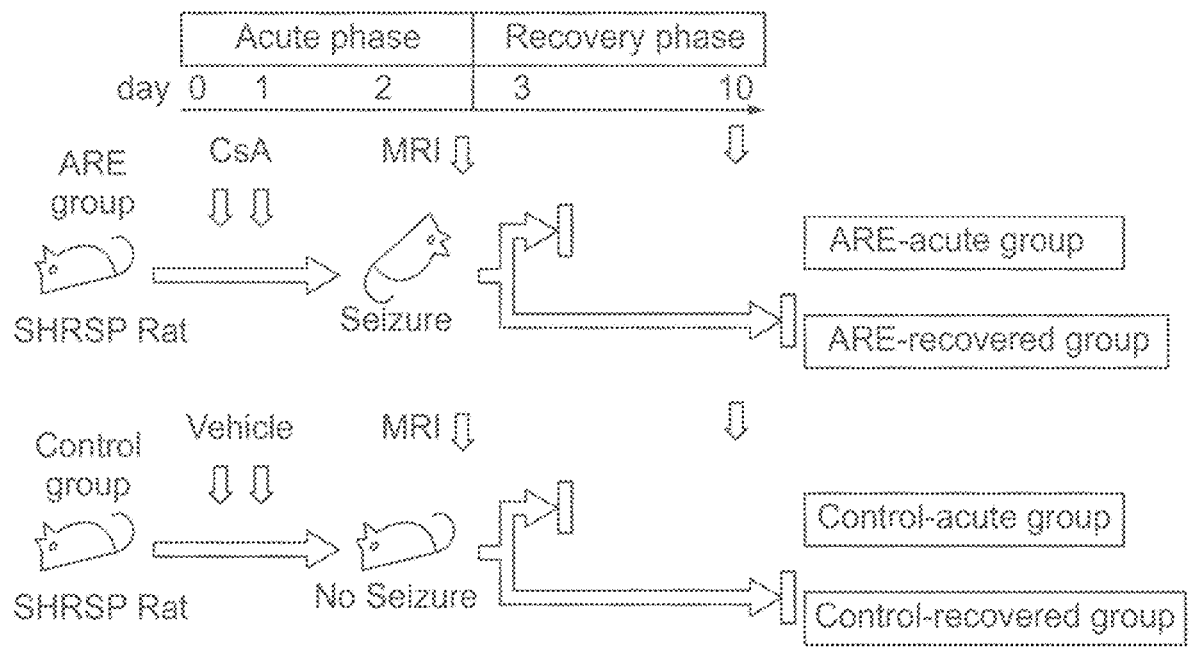
(FIG. 1A) Protocol for inducing acute reversible encephalopathy in rats. SHR-SP rats fed the JPD were treated with overdose cyclosporine A once daily for 2 days. Brain MRI was taken on day 3. CsA injection and JPD were discontinued to induce recovery, and the recovery-phase MRI was taken on day 10.
Figure 1B:
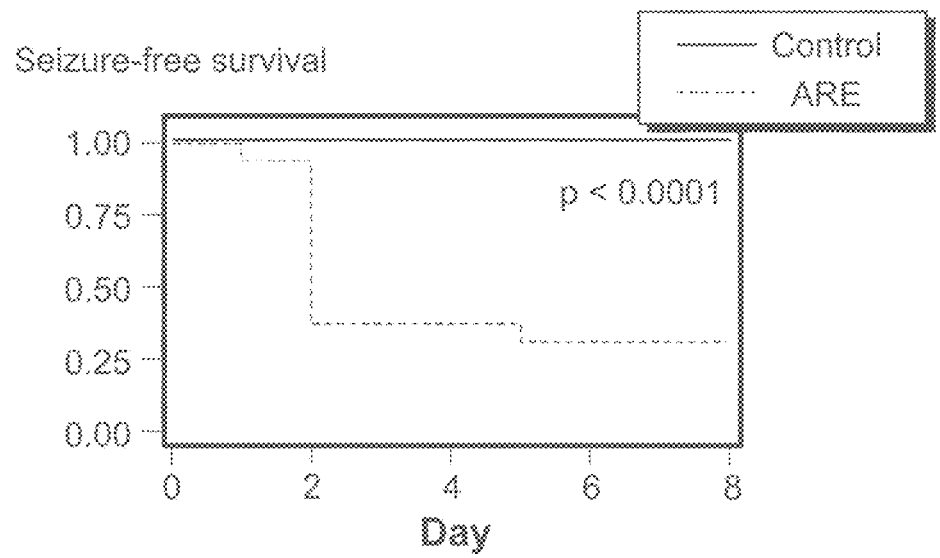
(FIG. 1B) Kaplan-Meier analysis for the occurrence of seizure.

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a representative basis for teaching one skilled in the art to variously employ the present invention in virtually any appropriately detailed method, structure or system. Further, the terms and phrases used herein are not intended to be limiting, but rather to provide an understandable description of the invention.

In one embodiment of the present invention, spontaneously hypertensive, stroke-prone rats were treated with high-dose cyclosporine A to induce an acute encephalopathy that mimicked posterior reversible encephalopathy syndrome. Recovery from the encephalopathy followed the cessation of cyclosporine A administration. The extent and recovery of neurological symptoms and brain lesions were monitored by neurological scores, behavioral tests, and magnetic resonance imaging. Blood-brain barrier leakage and myelin damage was histologically assessed.

Rats subjected to this acute encephalopathy model displayed deteriorating neurological symptoms and worsening scores in behavioral tests; these manifestations disappeared after recovery. In the acute phase of this encephalopathy, the fractional anisotropy and apparent diffusion coefficient increased in areas with IgG leakage. This increase of fractional anisotropy occurred in the absence of demyelination: fluid leakage into the myelinated space increased the axial, but not the radial, diffusivity, resulting in the increased fractional anisotropy. This increased fractional anisotropy returned to pre-encephalopathy values in the recovery-phase. As a result, the present invention uses fractional anisotropy increase as a marker for the reversibility of brain edema, which can delineate the brain areas for which recovery is possible.

In order to establish the acute reversible encephalopathy (ARE) model, 7-week-old spontaneously hypertensive, stroke-prone (SHR-SP) rats were fed the Japanese permissive diet (JPD; 16% protein, 0.75% potassium, 4.0% sodium; Ziegler Bros, Inc.) with 1% sodium chloride added to drinking water. At 9 weeks of age they were injected intraperitoneally with Cyclosporine A (CsA, Santa Cruz), dissolved in olive oil, or olive oil as vehicle, once daily for 2 days. In order to induce neurological symptoms, the doses of CsA (200 mg/kg/day) were set higher than those of the CsA nephrotoxicity rodent model according to preliminary studies. To investigate recovery from the ARE model, CsA injections and the JPD were discontinued on day 2, and rats were fed a regular diet with tap water for a week. The unilateral carotid arterial occlusion (UCAO)-JPD model was generated as previously described and used herein as a model for chronic and irreversible vasogenic edema. The middle carotid artery occlusion (MCAO) model was generated as previously described and used as a positive control for Fluoro-Jade staining.

The body weights of both the ARE and control group rats were measured daily. Systolic and diastolic blood pressures (SBP and DBP) were measured at two points; before starting the JPD and before starting the CsA or vehicle injections in order to confirm that the rats SBPs were above 200 mmHg, which is the physiological mean value for SHR/SP. Non-invasive blood pressure measurements were taken with a tail-cuff using the CODA system (Kent Scientific Inc.). Mean values of the blood pressure were calculated from seven measurements.

Neurological performance was assessed by clinical scoring of neuromuscular function daily Rotor-rod treadmill system tests (San Diego Instruments) and twice-weekly Catwalk XT (Noldus) experiments. Neurological symptoms were also assessed by the observation of seizures. The rotor-rod treadmill system tests were performed to detect motor deficits. Prior to the start of CsA treatments, rats were trained on the Rotor-rod cylinder and the latency to fall from the rod was averaged in three trials. Speed was gradually increased from 5 rpm to 40 rpm within 5 minutes. The CatWalk XT was used to detect subtle gait and motor. Prior to the start of the CsA treatments, the rats were trained to walk along the walkway in a dark room. Then, rats were subjected to gait assessment at days 0 and 2 for all animals, and day 9 for the recovery animals. One trial consisted of at least three runs and three successfully recorded runs were counted for analysis. Analyses for stance duration, stride length and body speed for each of four paws we preformed.

Histological analyses were prepared. In brief, rats were anesthetized with pentobarbital (50 mg/kg, intraperitoneally) and transcardially perfused with 2% Periodate Lysine Paraformaldehyde (PLP; 2% paraformaldehyde, 0.1 mol/L sodium periodate, 0.075 mol/L lysine in 100 mmol/L phosphate buffer, pH 7.3). Brains were removed, equilibrated to 2% PLP, cryoprotected with 30% sucrose, and embedded in OCT compound using 2-methylbutane cooled in liquid nitrogen. Brain tissues were then sectioned at 10 urn thickness. Kluver-Barrera (K&B) and Hematoxylin-Eosin (H&E) staining followed standard protocols. A TACS® 2 TdT DAB Kit (Trevigen Inc.) was used for TUNEL (terminal deoxynucleotide transferase-mediated deoxyuridine triphosphate nick-end labeling) staining and Fluoro-Jade C (Histo-Chem Inc.) was used for Fluoro-Jade staining. For immunohistochemistry, brain sections were stained using the following antibodies; rat anti-endothelial cell antibody-1 (RECA-1; 1:300, Abcam), glial fibrillary acidic protein (GFAP; 1:400, Sigma), anti CD11b (OX-42; 1:400, Accurate), myelin basic protein (MBP; 1:1000, Covance), and anti-Cy-3-conjugated affinity pure goat anti-rat IgG.

All animals underwent acute-phase MRI, and the recovery groups also underwent recovery phase MRI. MRI was performed on a 4.7 Tesla, 40 cm bore Bruker Biospec system, equipped with a 12 cm shielded gradient coil. Rats were placed prone on an animal bed, which was supported from the table outside the magnet. A 72 mm volume coil with a 2.5 cm actively decoupled brain surface coil was used for excitation and signal detection, respectively. Initial localizer images were acquired using a two-dimensional (2D) fast low-angle shot (FLASH) sequence with TR/TE 100/6 ms, matrix 128×128, FOV 8×8 cm, and one slice per orientation. Then, $T_2$-weighted ($T_2$w) MRI was performed using the following parameters: 2D rapid acquisition with relaxation enhancement (RARE), TR/TE 5000/65 msec, FOV 4×4 cm, slice thickness 1 mm, slice gap 1.1 mm, number of slices 12, matrix 256×256, number of averages 4. Magnetic resonance angiography (MRA) data were acquired using a FLASH-3D sequence, TR/TE 15/3 msec, matrix 256×256×128, number of average=1. Diffusion tensor MR images were obtained using echo-planar, diffusion tensor imaging (EP-DTI)

sequences with a TR of 3000 ms, a TE of 40 ms, and a b-value of 2000 mm$^2$/s with 30 diffusion gradient directions.

The acquired MR data were transferred to a dedicated computer workstation for post processing. ADC maps were generated from the raw DTI data to identify increased tissue water, which could be quantified as an increase in the ADC. FA, axial diffusivity (AD), radial diffusivity (RD) and mean diffusivity (MD) maps were calculated from the raw DTI data using ParaVision 5.1.

The areas of FA and ADC increase were determined from each of the slices. FA and ADC values in the white and gray matter were calculated in the slice that showed the largest changes for the CsA acute animals and these values were compared to the values from the same area and same slices from the CsA recovery and control animals. MRA 3D data were processed with ParaVision 5.1. Vessel areas (pixels) in 3D images from both CsA acute and control animals were calculated.

Figure 1C:
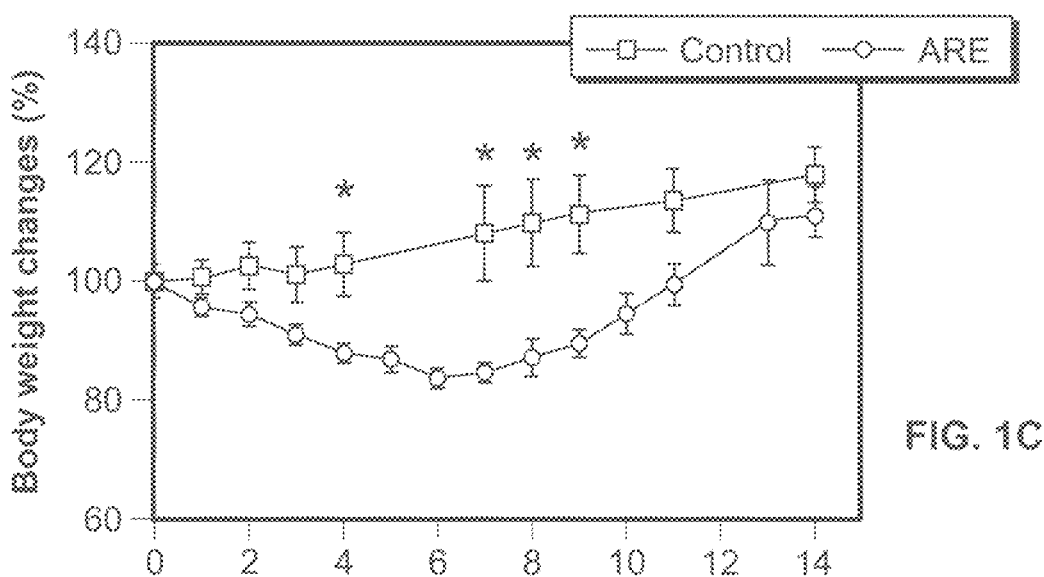
(FIG. 1C) Body weight changes of ARE model rats and their control.

A two-tailed Student's t test was used for determining the significance of differences between two groups, while a one-way ANOVA was used for multiple different groups. Occurrence of seizures was assessed by Kaplan-Meier analysis and differences were determined by the log rank test. Principal component analysis (PCA) and a biplot analysis were performed as described previously (Gabriel, 1971). Data were presented as mean and SEM. Statistical significance was An acute reversible encephalopathy (ARE) model was established according to the protocol shown in FIG. 1A. The ARE animals lost weight until 4 days after the cessation of the injections when they started to gain weight, whereas control group animals gained weight throughout the experimental period (FIG. 1C). The mean systolic blood pressure was found to be 160 mmHg for both the ARE and control group animals before the initiation of the JPD; this increased to 230 mmHg after the initiation of the JPD, but before the CsA injections in both 2 groups (Data not shown). Sixty-five percent of the ARE animals had seizures in the acute-phase, and most of these seizures occurred on day 2 (FIG. 1C).

Figure 1D:
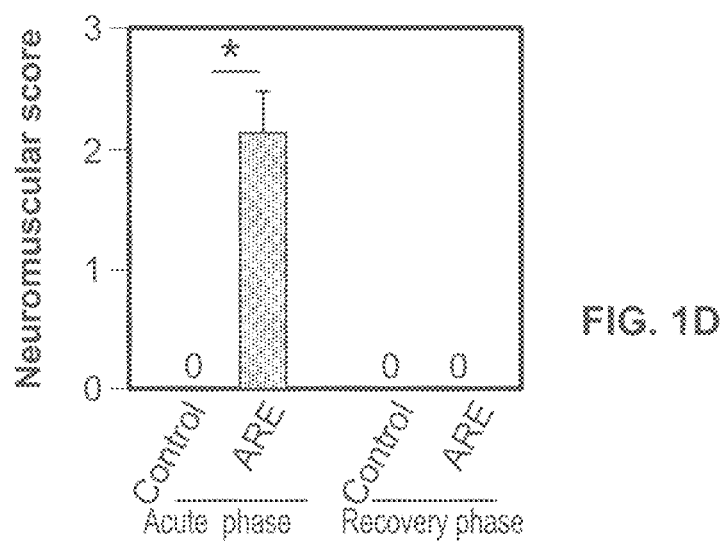
(FIGS. 1D and 1E) Neurological scores (FIG. 1D) and rotor-rods latencies (FIG. 1E) of ARE model rats and their control at baseline, and during the acute-, and recovery-phase.
Figure 1E:
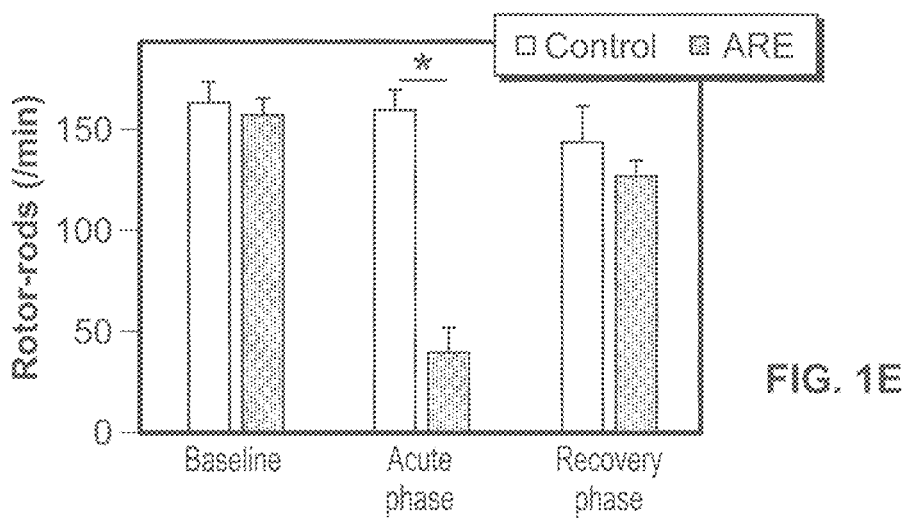
Figure 1F:
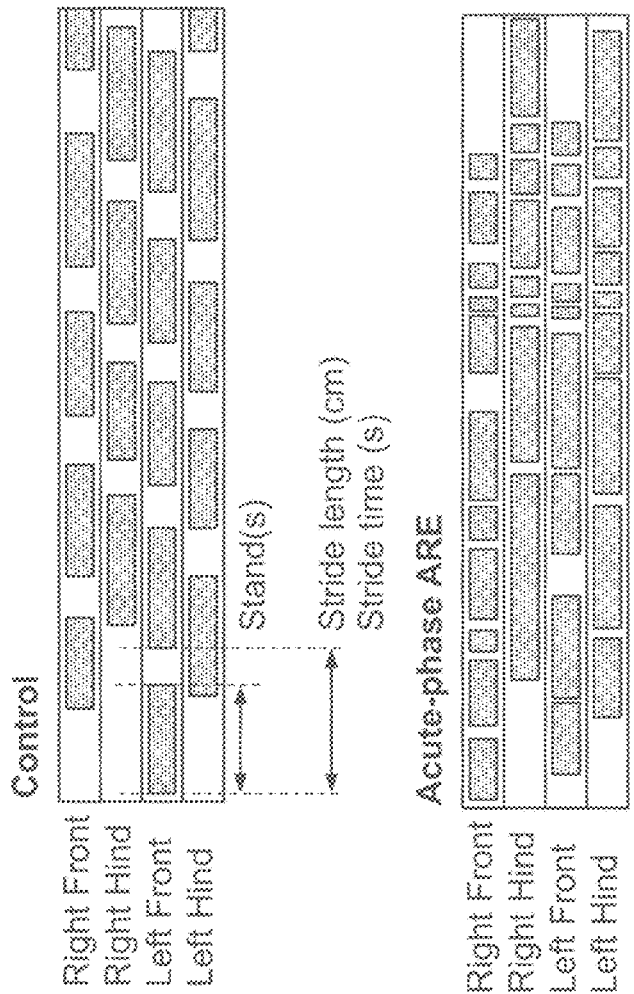
(FIG. 1F) Representative timing views of footprints from an acute-phase ARE rat and its control analyzed by CatWalk XT. Parameters used in (FIG. 1G) are shown.
Figure 1G:
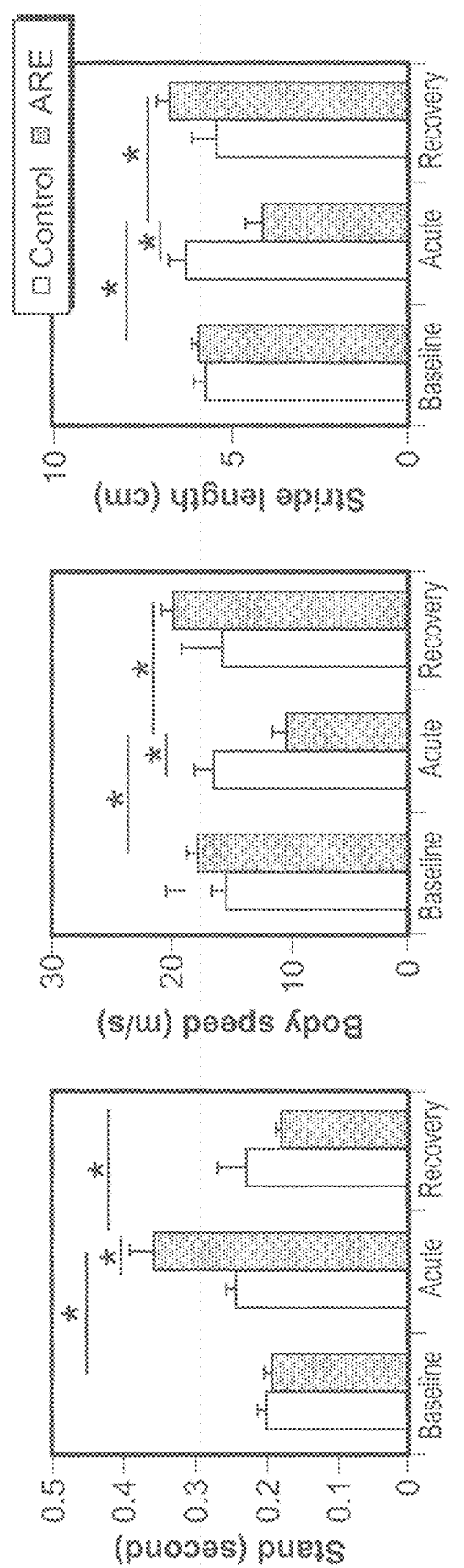
(FIG. 1G) Stand time, body speed and stride length of ARE model rats and their control at baseline, and during the acute-, and recovery-phase. Data from left hinds are shown. Data, means±SE, n=8 to 16, *P<0.05.

All of the ARE animals displayed neurological symptoms, while there were no neurological symptoms in the control animals (FIG. 1D). Rotor-rod latency was significantly decreased during the acute-phase of the ARE animals compared to the controls (FIG. 1E). Catwalk timing views revealed that walking patterns were impaired in the ARE acute animals compared to the control animals (FIG. 1F). Further analyses showed that stand time was prolonged, and that both body speed and stride length decreased in all 4 paws in ARE animals compared to the control group animals. (FIG. 1G for left hinds; data not shown for the other 3 paws.) These symptoms and test scores all resolved during the recovery-phase, in which animals did not receive any further doses of drug and were returned to the normal diet regimen (FIGS. 1D, E and G). Thus, the encephalopathy produced in this model was found to be reversible.

Figure 2A:
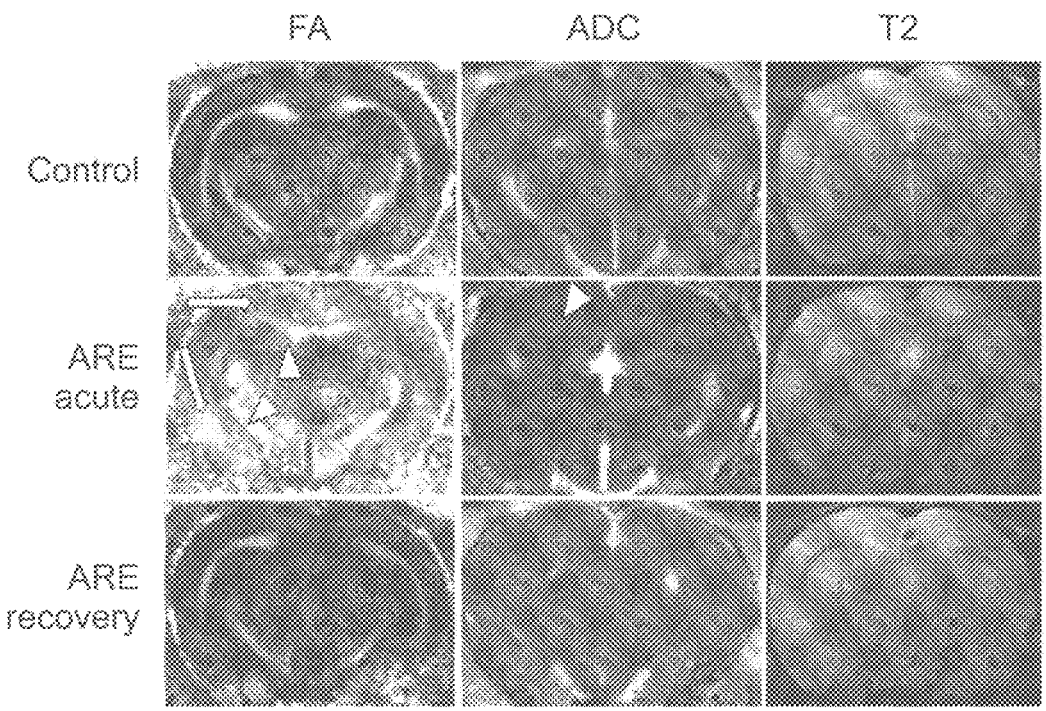
(FIG. 2A) Brain MRI (FA, ADC and T2 images) from acute- and recovery-phase of ARE model and their controls. Arrows and arrowheads indicate areas of increased FA in dorsal and ventral gray matter (DGM and VGM), and areas where both the FA and ADC increased in corpus callosum (CC) and internal capsule (IC), respectively.

In yet other embodiments of the present invention, MRI was used to examine the brain lesions produced in the ARE model. Both the FA and the ADC were seen to increase in acute-phase ARE animals (acute ARE) compared to control (FIG. 2A, left and middle columns). Although visual inspection of the T2w MR images did not show apparent changes in the MR signal intensities (FIG. 2A, right column), measurements of the pixel intensities revealed a statistically significant intensity increase in the brains of the acute ARE animals compared to the controls (data not shown) consistent with the induction of vasogenic edema in the ARE model. The ARE lesions were diffuse but were concentrated in MR slices 4 to 7 mm posterior to the Bregma, which are locations of the visual, auditory and motor cortices. An FA increase was seen in almost the entire white and gray matter (FIG. 2A). The observed ADC increase suggested the presence of vasogenic edema (FIGS. 2A & D). These increases in FA and ADC seen in acute-phase ARE animals resolved in the recovery phase (recovery ARE, FIG. 2A lower column).

Figure 2B:
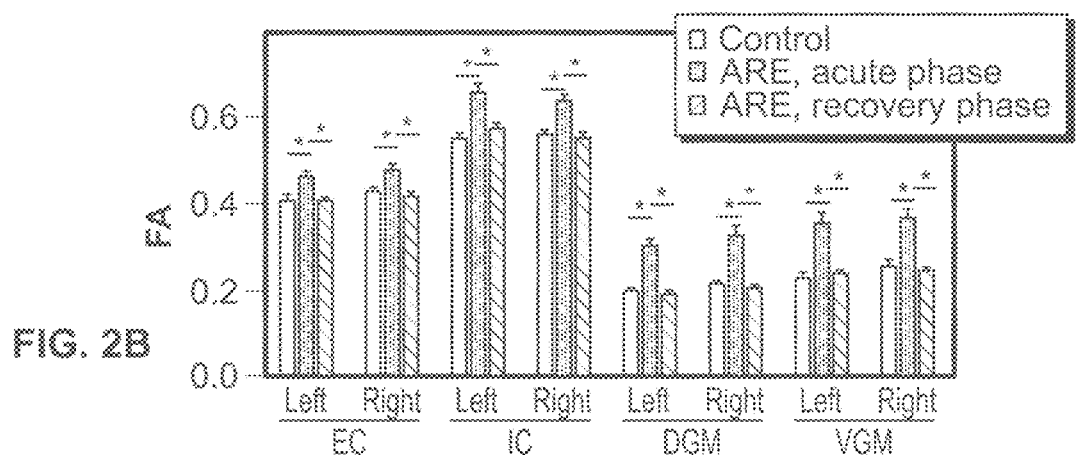

The MRI signals were quantified in each region of white and gray matter in both hemispheres. The FA increase seen in the acute ARE animals was confirmed in all the areas assessed (FIG. 2B). These FA values returned to normal in the recovery phase of the ARE model. The ADC values increased in all regions of the brains during acute ARE, reaching statistical significance in 6/8 regions (FIG. 2D) and these changes returned to normal during the recovery phase of the ARE model (FIG. 2D). These results suggest that both the FA and ADC values sensitively respond to ARE; these values increase in acute ARE and normalize after recovery.

Figure 2C:
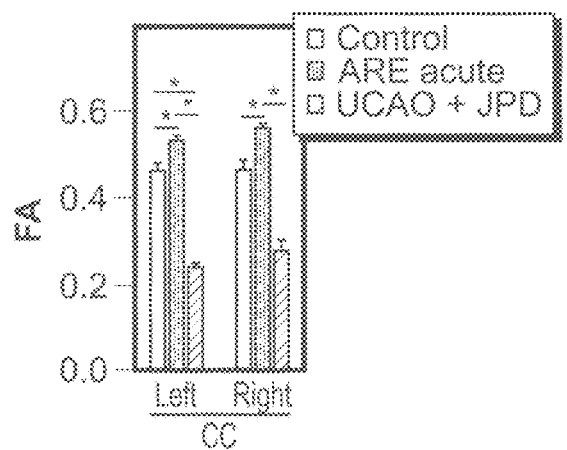

The observation that the diffusion properties of brain water return to normal supports the concept that the type of vasogenic edema seen in the ARE model is reversible. It was of great interest, therefore, to also examine an irreversible type of vasogenic edema. Therefore, FA/ADC values were compared for an ARE model with those from a chronic white matter injury model (UCAO-JPD animals) as a representative of irreversible vasogenic edema. The UCAO-JPD model has previously been shown to produce irreversible IgG leakage and demyelination in the corpus callosum (CC). As expected, a large increase of the ADC in UCAO-JPD animals was observed, suggesting the presence of vasogenic edema (FIG. 2E). On the contrary, the FA decreased in UCAO-JPD animals. (FIG. 2C) These results suggested that an FA increase is specifically seen in the acute-phase of reversible vasogenic edema.

MRA of the acute ARE animals revealed vasoconstriction and a narrowing of the distal vessel branches compared to the control animals (FIG. 3A) The areas of the vascular beds in acute ARE were significantly smaller than those of control animals (FIG. 3B). These changes were comparable to human cyclosporine A-induced encephalopathy.

A histological examination of the brain lesions of the ARE model animals was next performed. IgG leakage was detected within the injured area identified by MRI of acute-phase ARE (FIG. 4A, B middle columns), while H&E staining indicated a lack of hemorrhages (FIG. 4C). Fluoro Jade and TUNEL staining showed neither neuronal degeneration nor apoptotic cells in the brains from the acute ARE rats (FIGS. 4D & E). Furthermore, no apparent demyelination was observed in the acute ARE model, as assessed by K&B and MBP staining (FIGS. 4E & G, middle columns). In line with previously-reported PRES cases a slight astrocytosis was observed in the acute ARE model and also in recovery ARE compared with those of the controls, as assessed by GFAP staining (FIG. 4H). A slight microglial invasion was also seen in control animals as well as both acute and recovery ARE animals, because the control animals were also fed the JPD (FIG. 4I). The IgG leakage resolved and no further adverse histological findings were observed in the recovery-phase of the ARE model (FIGS. 4A & B, left column).

The mild astrocytosis and microglial invasion did not resolve in spite of the reversal of the IgG leakage. These results suggested that the brain lesions of the ARE model constitute a reversible vasogenic edema (FIG. 4J) without detectable demyelination, hemorrhage, or cell death.

Since the increases in the ADC and in the leakage of IgG both result from a compromise in the integrity of the blood-brain barrier, it was expected that these two disparate measures should be correlated. Potential correlations between the MRI and histological findings were investigated by measuring the ADC in the MRI slices and the IgG leakage areas in MRI-matched brain slices. IgG leakage occurred broadly in white matter tracts in both the acute ARE and UCAO-JPD models. IgG leakage was positively correlated with the ADC increase in both the acute ARE and UCAO-JPD models (FIG. 5A). However, the FA values changed in opposite directions in these two models: the FA increase seen in the acute ARE model totally distinguished this model from the UCAO-JPD model where the FA was found to decrease (FIG. 5B). This increased FA and ADC in the acute phase of the ARE model returned to normal in the recovery phase. These data implied that the FA, but not the ADC, reflected the reversibility of vasogenic edema.

Figure 6B:
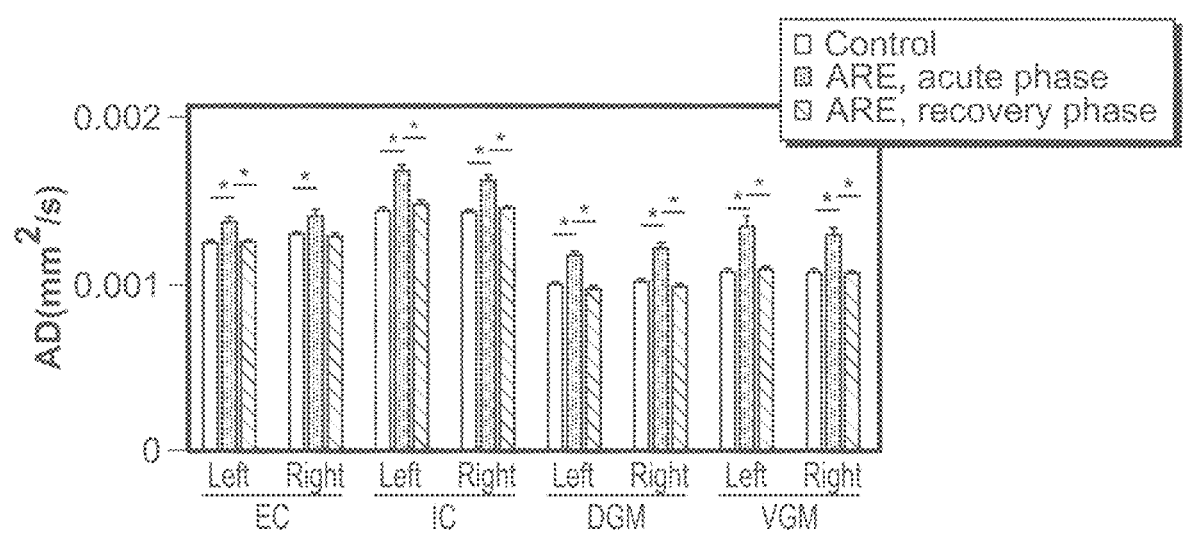
(FIG. 6B, FIG. 6C, FIG. 6D, FIG. 6E) AD (FIG. 6B and FIG. 6C) and RD (FIG. 6D and FIG. 6E) values in white matter and gray matter from acute- and recovery-phase of ARE model, UCAO-JPD and their control.
Figure 6C:
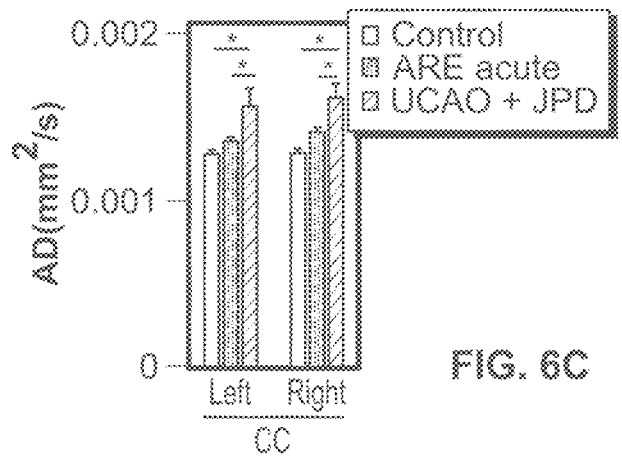

In addition to the FA, the diffusion tensor contains other information that allows for further characterization of tissue microstructural alterations during vasogenic edema. These consist of the axial (AD), radial (RD) and mean (MD) diffusivities (MD=ADC) (FIG. 6A) which are calculated by diagonalizing the diffusion tensor to produce its eigenvalues ($\lambda_1$, $\lambda_2$ and $\lambda_3$). The AD ($\lambda_1$) is assumed to be parallel to the axonal orientation. The FA is the degree of diffusion anisotropy calculated by using the DT eigenvalues: the FA value is 0 for isotropic diffusion, i.e., in the free water in the brain ventricles. Conversely, the FA value increases up to a maximum of 1.0 when the eigenvalues are significantly different from each other in magnitude.

In other aspects of the present invention, it was determined that the AD, but neither the MD nor the RD, increased in the acute ARE model (FIG. 6B-E, data not shown for MD). On the other hand, all the diffusivities, AD, MD and RD, increased in the UCAO-JPD model, (FIGS. 6C & E, data not shown for MD) suggesting the presence of demyelination and/or axonal damage in this model that is distinct from the ARE model. A biplot display of the principal component analysis (FIG. 6F) revealed that the AD value distinguished the acute ARE model from the controls, after the exclusion of the UCAO-JPD model by its MD and RD. The observed diffusivity differences between these two models represent difference in the profiles of myelination; leaked fluid can diffuse only in the direction parallel to axons in acute ARE because of the limited space in the presence of myelin, whereas it can freely diffuse in demyelinated space in the UCAO-JPD model. This anisotropic diffusion is the cause of the FA increase detected in acute ARE, while increased isotropic diffusion led to an FA decrease in the UCAO-JPD model. The AD increase seen in the acute phase of ARE returned to normal in the recovery phase of ARE, reflecting the reabsorption of the leaked IgG-containing fluid.

These results suggest that fluid leakage in vasogenic edema is the cause of the FA increase in white matter without demyelination. The increased axial, but not radial, diffusivity due to IgG leakage in the myelinated space causes the FA to increase in acute ARE. Though the mechanism is unclear, the increase of AD without significant changes in RD was also seen in gray matter of the acute ARE model.

In other aspects the present invention provides a methodology that uses MRI and histology to demonstrate that IgG leakage out of the vessels paralleled an FA increase during the acute phase of reversible vasogenic brain edema. Increased axial, but not radial, diffusivity of water due to leakage into the myelinated space was the cause of this observed FA increase in the ARE model. The present ARE model showed FA increases in both white and gray matter in the absence of demyelination. The FA and IgG leakage returned to normal values upon resolution of the encephalopathy.

Most of the DTI studies reported thus far for various brain injuries in patients and in animal models have reported a decrease in FA. These decreases in the FA were attributed to the demyelination and/or axonal damage present in several disease states and models of chronic white matter injuries, i.e., stroke, small vessel disease, multiple sclerosis, amyotrophic lateral sclerosis and traumatic brain injury (TBI).

On the other hand, a limited number of studies have reported an FA increase. These could previously be divided into two pathophysiological categories. The first consists of studies finding an FA increase along with a decrease in the ADC, as seen, for example, in cytotoxic edema resulting from the hyperacute stage of stroke (within 3 to 4.5 hours from stroke onset). The second category is characterized by findings of an FA increase and only a slight increase in the ADC, as observed in mild TBI patients due to astrocytosis.

The simultaneous significant increases of the FA and the ADC, found, in the absence of demyelination, during the vasogenic edema of the present ARE model, clearly distinguish it from other vasogenic edemas which display a decreased FA accompanied by demyelination. This FA increase accompanied by fluid leakage in the ARE model forms a third pathophysiological category alongside the previous two pathologies that show an increase in the FA.

Figure 7:
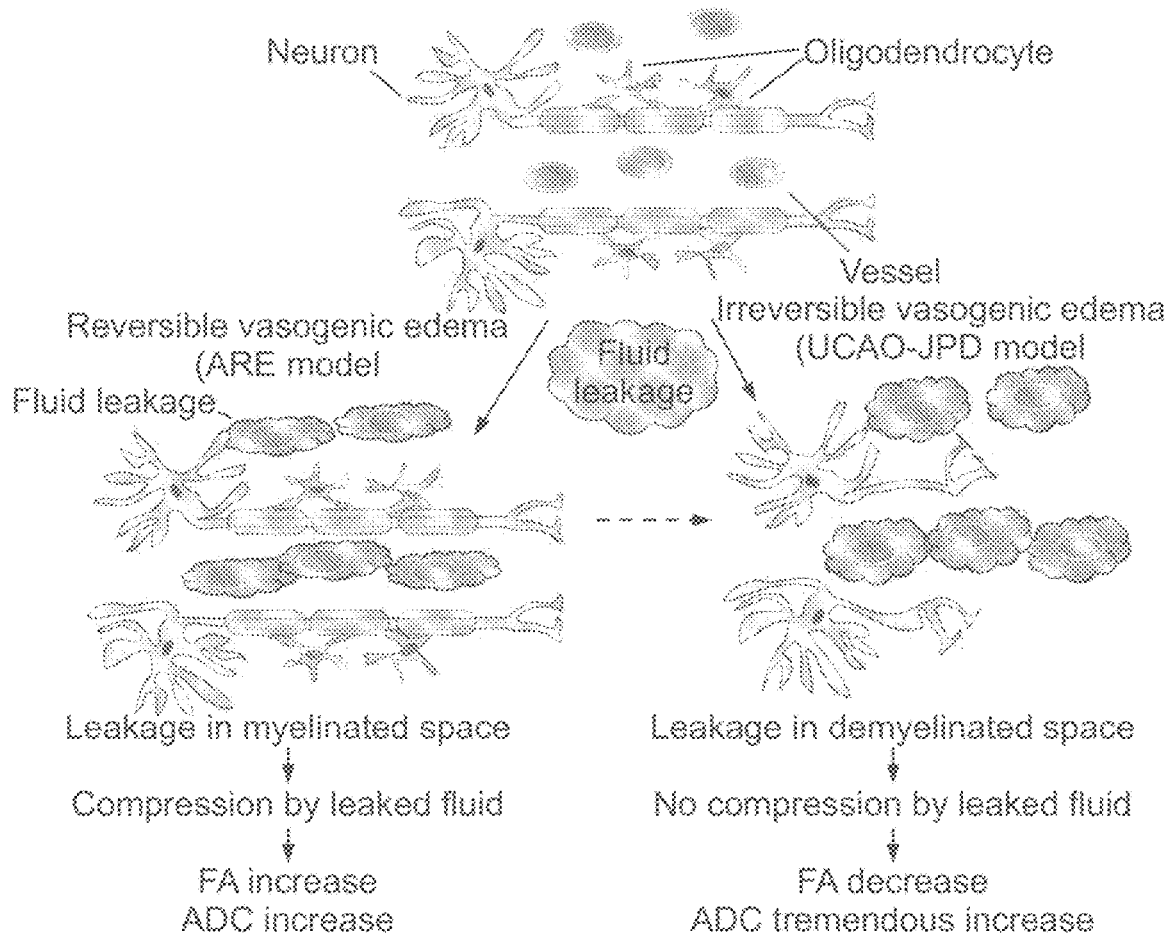
FIG. 7. Microstructural changes of brain white matter in reversible and irreversible vasogenic edema, which form the basis for the leakage hypothesis. In reversible vasogenic edema fluid leaked from vessels compresses the myelin structures. Then diffusivity perpendicular to the axons (RD) decreases and diffusivity parallel to the axons increases. This results in an FA increase. In irreversible vasogenic edema, degradation of myelin structures expands the spaces between axons. This results in an increase in the diffusivities in all directions, and therefore, results in a FA decrease. The dashed arrow indicates postulated prognosis in the absence of intervention.
Figure 8:
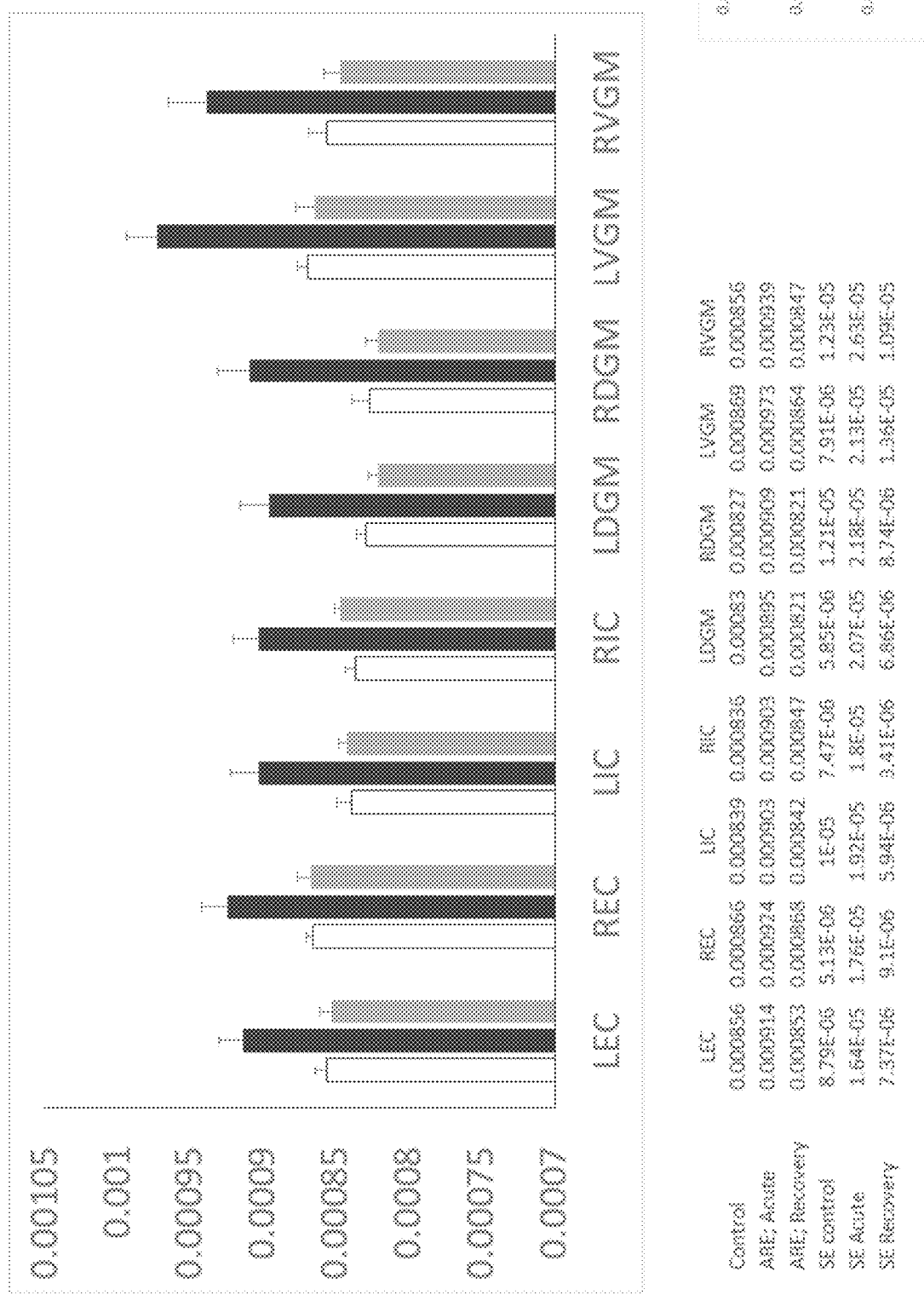
FIG. 8. Table 2 shows a summary of MRI apparent diffusion coefficient changes.
Figure 9:
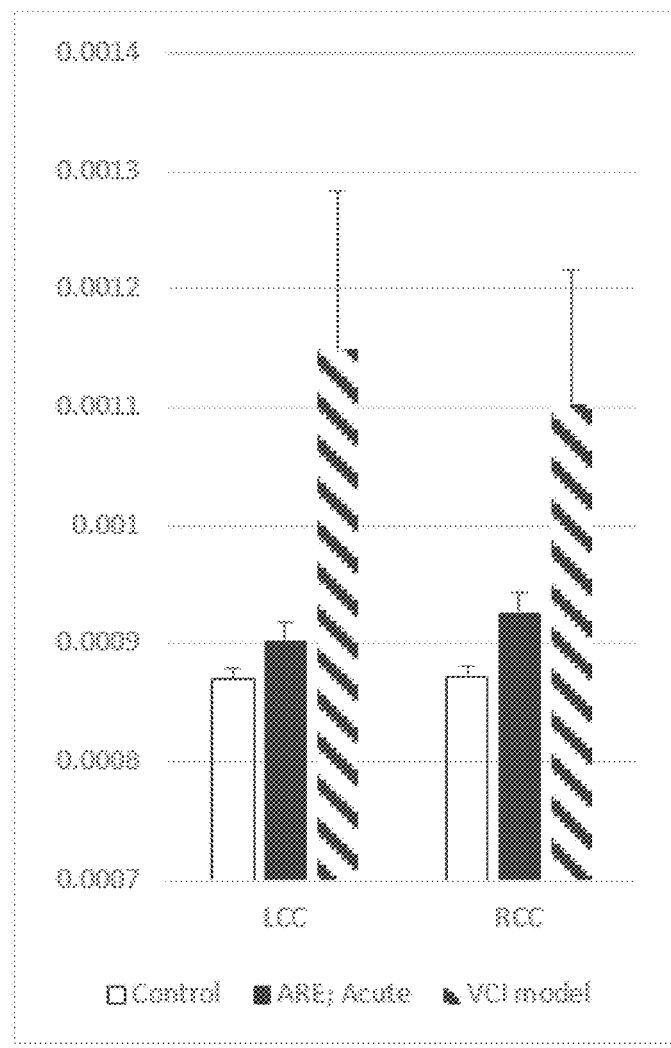
FIG. 9. Table 3 shows a summary of MRI fractional apparent diffusion coefficient changes in ARE and VCI.
Figure 10:
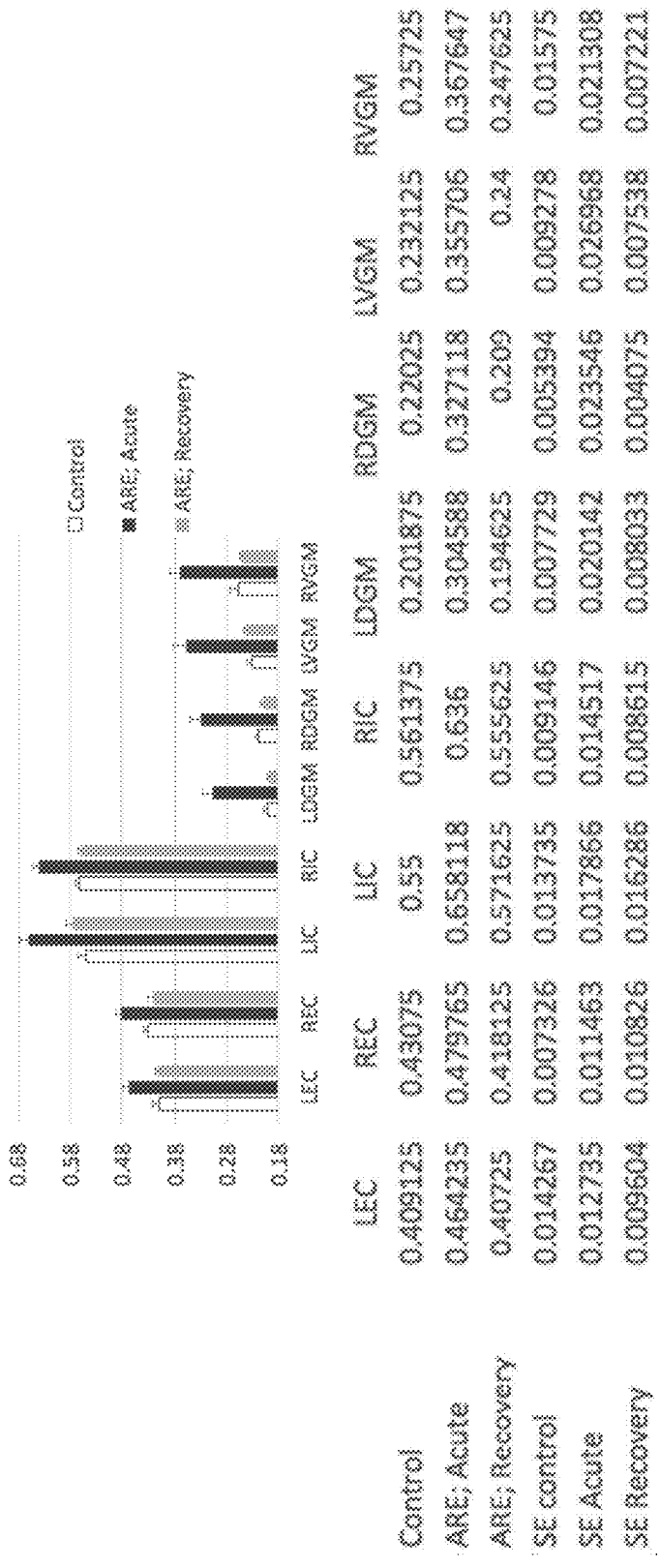
FIG. 10. Table 4 shows a summary of fractional anisotropy changes in ARE during acute and recovery phase.
Figure 11:
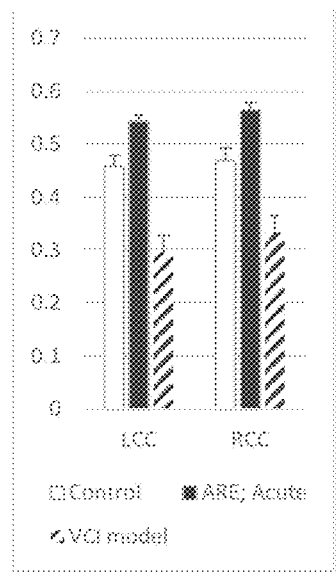
FIG. 11. Table 5 shows fractional anisotropy changes in ARE during the acute phase and irreversible vascular occlusion model.

In other aspects, the present invention is based on water leakage to explain the FA changes seen in reversible vasogenic edema in the ARE model. As shown in FIG. 5, increases in both the ADC and the FA correlated with the severity of the IgG leakage in the ARE model. These results may be from the leakage from blood vessels of plasma components (water) that accumulate between the myelin sheaths and compress the myelinated axons. This restricts the diffusion of water perpendicular to the axon forcing the water to move parallel to the axon (FIG. 7). The reversibility of the IgG leakage was also confirmed by normalization of the FA and the ADC.

However, in irreversible vasogenic edema with demyelination, i.e., the UCAO-JPD model, the FA does not follow this same pattern with the IgG leakage. An increase in the RD and an FA decrease measured by DTI has been reported to reflect dysmyelination and demyelination and/or axonal damage.

This different behavior of the FA value in irreversible vasogenic edema may be because the FA change is induced by other histological changes; i.e. demyelination and/or axonal damage. In the presence of demyelination or axonal damage, the space between the myelin sheaths and fibers expands and water's diffusion becomes more isotropic, leading to a decrease in the FA an increase in the RD, as seen in the UCAO-JPD model (FIGS. 2 & 6). In addition, due to the enlarged space, IgG leakage does not contribute to this increased water diffusivity (FIG. 7).

Figure 6D:
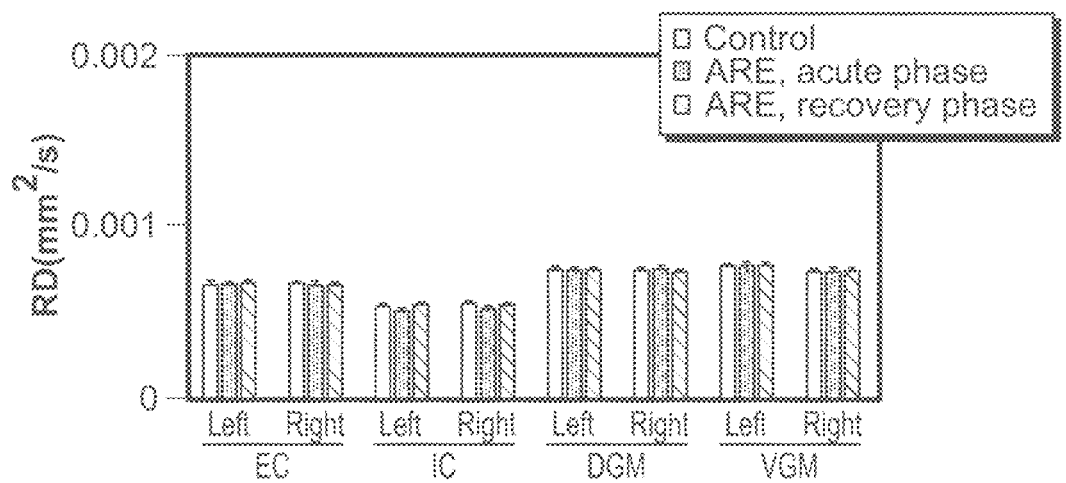
Figure 6E:
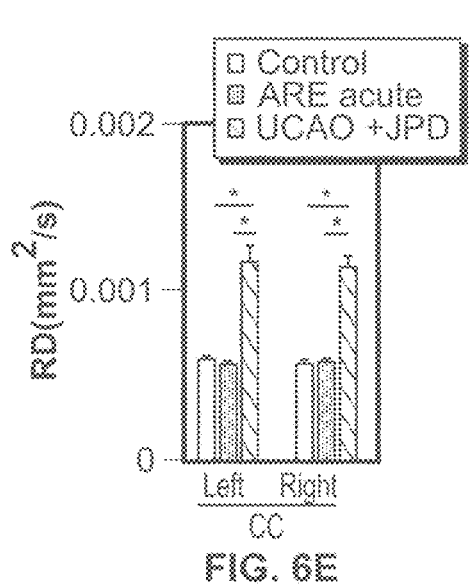
Figure 6F:
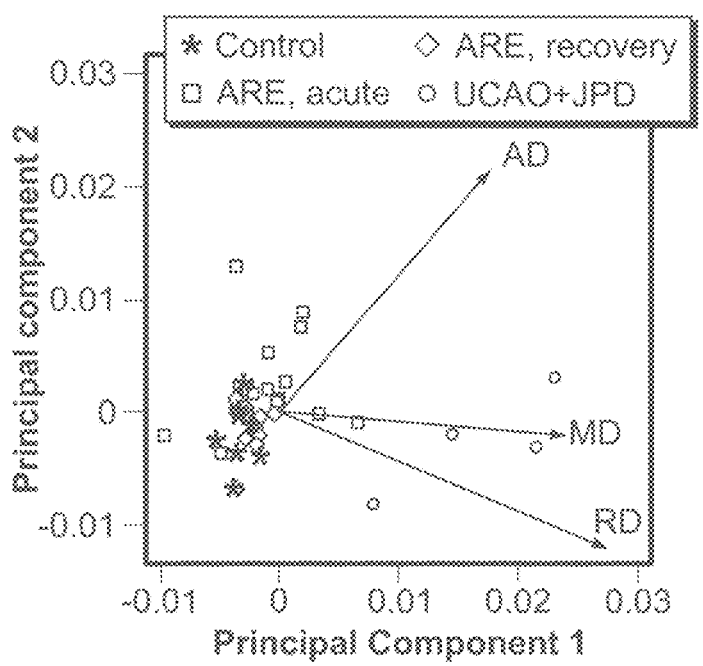
(FIG. 6F) Also shown is a biplot visualization of AD, RD and MD for ARE, UCAO-JPD and control. A model for the microstructural changes of brain white matter in reversible and irreversible vasogenic edema (leakage hypothesis). In reversible vasogenic edema fluid leaked from vessels compresses the myelin structures. Then diffusivities perpendicular to axons (RD) decrease and diffusivity parallel to axons increases. This results in an FA increase. In irreversible vasogenic edema, degradation of myelin structures expands the spaces between axons. This results in an increase in the diffusivities in all directions, and therefore, results in FA decrease. The dashed arrow indicate postulated prognosis in the absence of intervention.

Taken together, the observations in the present ARE model of an invariant RD together with an FA/ADC increase provide additional support. The increased FA in the ARE model results from directionally-constrained fluid movement within the intact axonal myelin structure. Though not significant, the white matter in the ARE model showed a small, but consistent RD decrease in the acute-phase (FIG. 6D). The RD decreases because fluid leakage compresses the axon, restricting diffusion of water perpendicular to axon and lowering the two radial diffusion tensor eigenvalues, $\lambda_2$, $\lambda_3$ (FIG. 6). This phenomenon was also observed during the cytotoxic edema accompanying the hyper acute-phase of stroke. The observed normalization of the FA values in the recovery phase of the ARE model also supports this leakage hypothesis; the FA returns to normal when the leaked plasma components are reabsorbed in the absence of demyelination, cell degeneration, or proliferation.

In yet other embodiments of the present invention, FA images may be added to conventional MRI protocols in order to discriminate the hyperacute phase from the chronic phase in the cytotoxic edema arising from a stroke. FA images could also be valuable for differentiating the reversible from the irreversible stages in vasogenic edema (Table 1). Similar FA increases are found in both hyperacute cytotoxic edema and reversible vasogenic edema. However, the behavior of the ADC differs and these differences are clinically used to discriminate vasogenic edema from cytotoxic edema. Clinically, the hyperacute stage of stroke, within the golden hour, and PRES are in this category.

On the other hand, cases where the FA decreases include the chronic stage of cytotoxic edema and permanent vasogenic edema; both of these situations involve demyelination, axonal damage and a poor prognosis. Clinical examples of these conditions are, for the former, the chronic stage of stroke core lesions, and for the latter, chronic white matter disease and chronic multiple sclerosis lesions. The present ARE model and the UCAO-JPD model are representative animal models for these prognostically-opposite vasogenic edemas; acute reversible and chronic irreversible, respectively. Unlike cytotoxic edema, these two conditions in vasogenic edema have not been proved to be chronologically-linked. As a result, in the absence of intervention, reversible vasogenic edema will progress to irreversible edema (Dashed arrow in FIG. 7).

Although the mechanism proposed above for the increase in FA in the white matter has been explained, the FA increase found in the gray matter is more difficult to explain. Other investigators have reported that the FA increased in the gray matter of the basal ganglia in a patient with a subdural hematoma; this FA increase resolved after evacuation of the hematoma (Osuka et al., 2012). In cases of mild TBI in humans and in animal models, the FA also increased in the cortex of the pertinent lesion (Budde et al., 2011; Bouix et al., 2013). The proposed mechanisms were compression by the hematoma for the former case and gliosis for the latter.

In an ARE model of the present invention, a slight astrocytosis was found, which did not resolve with the normalization of the FA increase, suggesting that gliosis per se was not a likely reason for the FA increase. Therefore, the FA increase seen in the gray matter of the ARE model are due to compression from edematous white matter. This proposal is supported by the observation that the most severe reversible FA increases were mainly seen next to the boundary of the skull (data not shown).

The ARE model of the present invention recapitulated many salient features of human PRES. Seizures are a major manifestation of PRES. Most of these patients fully recovered without sequelae. Autopsy studies of PRES patients showed several histological manifestations that were very similar to those found in the ARE model. These include (FIG. 4) an opening of the BBB, reactive astrocytosis, microglial invasion, and demyelination without a loss of oligodendrocytes, or no demyelination. MRI studies of PRES patients have also revealed characteristics of reversible vasogenic edema congruent with the findings; hyperintensities are seen in $T_2w$ MR images along with concomitant increases in the ADC, most prominently in the occipital or occipito-parietal lobes. MRA of PRES patients showed a narrowing or beaded appearance for the vessels, reflecting an underlying vasospasm and/or vasoconstriction, findings which disappeared upon resolution of the encephalopathy as seen with repeated. A slight hyperintensity on $T_2w$ MRI, an ADC increase and a severe narrowing and lack of distal branch arteries, observed by MRA, were detected in the present ARE model. The distribution of lesions in the present ARE model was primarily diffuse, but tended to favor the occipito-parietal area (Bregma −4 to −6 mm) and involved both gray and white matter.

Taken together, the features of the model present a reversible vasogenic edema which closely resembled PRES. Although, based on present knowledge, FA images in PRES patients have yet to be reported, an FA increase with subsequent resolution was detected with the model, and we believe that it would be worth searching for a similar reversible FA increase in PRES patients.

The mechanism underlying this reversible BBB opening/leakage is not completely clear, but a likely contributing factor is damage to the endothelium by CsA. PRES usually has underlying conditions such as hypertension, immune disorders, transplantation or eclampsia. Most of these risk factors are associated with endothelium activation or injury, vascular instability, or systemic hypoperfusion, and share a common pathophysiology with the SHRSP rats used here. Additionally, SHRSP rats have poor tight junction function and a leaky BBB. Indeed, SHRSP rats usually develop neurological complications spontaneously after 16 weeks of age. Histological studies on 10 month old, stroke-free SHRSP rats revealed an absence of astrocytosis, microglial invasion, or myelin basic protein expression changes. MRI studies revealed no white matter lesions, no signal abnormalities in $T_2w$ MR images and no FA decrease. On the other hand, SHRSP rats fed on a JPD from 8-10 weeks-old had abnormal MR images seven weeks after the switch to the JPD. These facts explain why the present model showed only minor astrocytosis and microglial invasion; for the younger SHRSP rats two weeks on the JPD diet was insufficient to cause brain abnormality. It was concluded that the endothelial dysfunction produced by the CsA, as well as the genetic background (SHRSP) of the animals, were the mechanisms underlying reversible vasogenic edema, instead of abnormalities of astrocytes and microglia.

Fluid leakage due to vasogenic edema was the cause of the FA increase observed in white matter, and that this leakage, along with the symptoms, histological and MRI findings was reversible. The ability to detect this reversible vasogenic edema with MR-DTI enables clinicians to locate areas of the brain or predetermined regions of the brain for which intervention and rescue may be possible, such as areas in the penumbra of a stroke and in encephalopathy/encephalitis lesions. The findings here provide additional support for the concept that an FA increase is a marker for reversibility and conserved myelination.

TABLE 1

Summary of MRI signal changes in cytotoxic (sodium/potassium exchange) and vasogenic (pressure) edema.

| | Cytotoxic edema | | Vasogenic edema | |
|---|---|---|---|---|
| | Hyper acute | Chronic | Reversible | Irreversible |
| T2 | ↑↑ | ↑↑ | ↑ | ↑↑ |
| ADC | ↓ | ↑ | ↑ | ↑↑ |

TABLE 1-continued

Summary of MRI signal changes in cytotoxic (sodium/potassium exchange) and vasogenic (pressure) edema.

| | Cytotoxic edema | | Vasogenic edema | |
|---|---|---|---|---|
| | Hyper acute | Chronic | Reversible | Irreversible |
| FA | ↑ | ↓ | ↑ | ↓ |
| RD | →or↓ | ↑ | →or↓ | ↑ |

As shown above in Table 1, ↑↑ equals large increases in intensity from normal. ↑ means intensity increases slightly from normal. → or ↓ means stable or a slight decrease from normal. ↓ means a slight decrease from normal.

As shown above and also in Table 1, a reversible pathological condition in a brain such as vasogenic edema in brain regions of interest may be diagnosed for a mammalian subject that has suffered vasogenic edema by acquiring over a predetermined period of time a plurality of magnetic resonance imaging (MRI) images for each brain region of interest. The MRI images are analyzed to obtain quantitative measurements of the fractional anisotropy (FA) for each brain region of interest over the predetermined period of time. Brain regions of interest that have reversible vasogenic edema have measured FA that increases and then decreases over the predetermined period of time. As is also shown, irreversible damage is indicated by a decrease in FA over observed period of time.

As shown above and also in Table 1, in yet another embodiment of the present invention, in addition to analyzing the changes in FA, an additional analysis that may be performed, with or without the FA measurement, to determine whether a brain region of interest has reversible vasogenic edema includes the steps of acquiring a plurality of T2 weighted images over the predetermined period of time. For each brain region of interest, the T2 weighted images are analyzed to obtain quantitative measurements of the intensity of each image for each brain region of interest over the predetermined period of time. Brain regions of interest that have reversible vasogenic edema show a measured T2 weighted image intensity that increases and then decreases over the predetermined period of time.

As shown above and also in Table 1, in yet another embodiment of the present invention, in addition to analyzing the changes in FA and/or T2 weighted image intensity, an additional analysis that may be performed, with or without the FA and/or T2 weighted image intensity measurements, to determine whether a brain region of interest has reversible vasogenic edema includes the steps of acquiring a plurality of apparent diffusion coefficient values over the predetermined period of time for each brain region of interest. The apparent diffusion coefficient values are analyzed to obtain quantitative measurements of the diffusion coefficient value for each brain region of interest over the predetermined period of time. Brain regions of interest that have reversible vasogenic edema show measured diffusion coefficient values that increase and then decrease over said predetermined period of time.

As shown above and also in Table 1, in yet another embodiment of the present invention, in addition to analyzing the changes in FA, T2 weighted image intensity and/or diffusion coefficient values, an additional analysis that may be performed, with or without the FA, T2 weighted image intensity and/or diffusion coefficient values, to determine whether a brain region of interest has reversible vasogenic edema includes the steps of acquiring a plurality of radial diffusivity values over the predetermined period of time for each brain region of interest. The radial diffusivity values are analyzed to obtain quantitative measurements of the radial diffusivity value for each brain region of interest over the predetermined period of time. Brain regions of interest that have reversible vasogenic edema show measured radial diffusivity values that remain the same or decrease over said predetermined period of time.

As shown above, FA may be used to accurately predict recovery of the brain, or predetermined regions of the brain, after injury, trauma, biological events and pathological events. For example, as shown in Table 6, although changes in both ADC and FA occur, the data shows that changes in FA out perform changes in ADC establishing that the sensitivity of FA is superior to ADC.

TABLE 6

Summary of percent changes in ADC and FA in dorsal white matter (DWM) and dorsal gray matter (DGM).

| | ARE | % Change <DWM> | % Change <DGM> | Ratio <GM>/<WM> |
|---|---|---|---|---|
| | ADC | 7.1 | 10.3 | 1.5 |
| | FA | 14.6 | 50.7 | 3.5 |
| Ratio | (FA)/(ADC) | 2.1 | 4.9 | |

As shown, the FA changes in gray matter are the most sensitive measure of edema and recovery. As shown, the most sensitive measure of the edema is the FA of the Gray Matter (GM) where (FA)=51%. It was also found that the change in FA is 2 to 5 times greater than that seen for the ADC for either White (WM) or Gray Matter (GM). These data support the use of FA as the best measure rather than ADC.

While the foregoing written description enables one of ordinary skill to make and use what is considered presently to be the best mode thereof, those of ordinary skill will understand and appreciate the existence of variations, combinations, and equivalents of the specific embodiment, method, and examples herein. The disclosure should therefore not be limited by the above described embodiments, methods, and examples, but by all embodiments and methods within the scope and spirit of the disclosure.

What is claimed is:

1. A method for determining for a mammalian subject that has suffered vasogenic edema whether the subject has brain regions of interest having reversible or irreversible vasogenic edema comprising the steps of: acquiring over a predetermined period of time a plurality of magnetic resonance imaging (MRI) images for each brain region of interest; analyzing said MRI images to obtain quantitative measurements of the fractional anisotropy (FA) for each brain region of interest over said predetermined period of time; and determining that brain regions of interest have reversible vasogenic edema when said measured FA increases and then decreases over said predetermined period of time.

2. The method of claim 1 further including the steps of acquiring a plurality of T2 weighted images over said predetermined period of time for each brain region of interest, analyzing said T2 weighted images to obtain quantitative measurements of the intensity of each image for each brain region of interest over said predetermined period of time, and determining that brain regions of interest have reversible vasogenic edema when said measured T2 weighted image intensity increases and then decreases over said predetermined period of time.

3. The method of claim 2 further including the steps of acquiring a plurality of apparent diffusion coefficient values over said predetermined period of time for each brain region of interest, analyzing said apparent diffusion coefficient values to obtain quantitative measurements of the diffusion coefficient value for each brain region of interest over said predetermined period of time, and determining that brain regions of interest have reversible vasogenic edema when said measured apparent diffusion coefficient values increase and then decrease over said predetermined period of time.

4. The method of claim 3 further including the steps of acquiring a plurality of radial diffusivity values over said predetermined period of time for each brain region of interest, analyzing said radial diffusivity values to obtain quantitative measurements of the radial diffusivity value for each brain region of interest over said predetermined period of time, and determining that brain regions of interest have reversible vasogenic edema when said measured radial diffusivity values remain the same or decrease over said predetermined period of time.

5. The method of claim 1 wherein FA increases by 10 to 50 percent in white and gray matter and returns to original levels.

6. The method of claim 1 wherein FA is measured to indicate the acute phase of reversible vasogenic brain edema.

7. The method of claim 1 wherein FA is measured to determine damage to both white and gray tracts of the brain.

8. The method of claim 1 wherein FA is measured to determine damage to white tracts of the brain.

9. The method of claim 1 wherein FA is measured to determine damage to gray tracts of the brain.

10. The method of claim 1 wherein FA is measured to examine brain lesions.

11. The method of claim 1 wherein FA is measured to determine IgG leakage.

12. The method of claim 1 wherein FA is to determine leakage from blood vessels of plasma components that accumulate between the myelin sheaths and compress the myelinated axons.

13. The method of claim 1 wherein FA is measured by MR-DTI to detect reversible vasogenic edema.

14. The method of claim 1 wherein FA is measured to locate areas of the brain intervention.

15. A methodology that measures FA increase as a marker for reversibility and conserved myelination.

16. A method for determining for a mammalian subject that has suffered vasogenic edema whether the subject has brain regions of interest having reversible or irreversible vasogenic edema comprising the steps of: acquiring over a predetermined period of time 1) a plurality of magnetic resonance imaging (MRI) images for each brain region of interest; analyzing said MRI images to obtain quantitative measurements of the fractional anisotropy (FA) for each brain region of interest over said predetermined period of time; 2) acquiring a plurality of T2 weighted images over said predetermined period of time for each brain region of interest, analyzing said T2 weighted images to obtain quantitative measurements of the intensity of each image for each brain region of interest over said predetermined period of time; 3) acquiring a plurality of apparent diffusion coefficient values over said predetermined period of time for each brain region of interest, analyzing said apparent diffusion coefficient values to obtain quantitative measurements of the diffusion coefficient value for each brain region of interest over said predetermined period of time; 4) acquiring a plurality of radial diffusivity values over said predetermined period of time for each brain region of interest, analyzing said radial diffusivity values to obtain quantitative measurements of the radial diffusivity value for each brain region of interest over said predetermined period of time; and 5) determining that brain regions of interest have reversible vasogenic edema when said measured FA, said T2 weighted image intensity and said diffusion coefficient values increase and then decreases over said predetermined period of time and said measured radial diffusivity values remain the same or decrease over said predetermined period of time.

17. The methods of claim 16 wherein FA increases by 10 to 50 percent in white and gray matter and returns to original levels.

18. A method for determining whether brain regions of interest having reversible or irreversible pathology comprising the steps of: acquiring over a predetermined period of time a plurality of magnetic resonance imaging (MRI) images for each brain region of interest; analyzing said MRI images to obtain quantitative measurements of the fractional anisotropy (FA) for each brain region of interest over said predetermined period of time; and determining that brain regions of interest have reversible pathology when said measured FA increases and then decreases over said predetermined period of time.

19. The method of claim 18 further including the steps of acquiring a plurality of T2 weighted images over said predetermined period of time for each brain region of interest, analyzing said T2 weighted images to obtain quantitative measurements of the intensity of each image for each brain region of interest over said predetermined period of time, and determining that brain regions of interest have reversible pathology when said measured T2 weighted image intensity increases and then decreases over said predetermined period of time.

20. The method of claim 19 further including the steps of acquiring a plurality of apparent diffusion coefficient values over said predetermined period of time for each brain region of interest, analyzing said apparent diffusion coefficient values to obtain quantitative measurements of the diffusion coefficient value for each brain region of interest over said predetermined period of time, and determining that brain regions of interest have a reversible pathology when said measured apparent diffusion coefficient values increase and then decrease over said predetermined period of time.

21. The method of claim 20 further including the steps of acquiring a plurality of radial diffusivity values over said predetermined period of time for each brain region of interest, analyzing said radial diffusivity values to obtain quantitative measurements of the radial diffusivity value for each brain region of interest over said predetermined period of time, and determining that brain regions of interest have a reversible pathology when said measured radial diffusivity values remain the same or decrease over said predetermined period of time.

22. The method of claim 18 wherein FA increases by 10 to 50 percent in white and gray matter and returns to original levels.

23. The method of claim 1 wherein FA increases by 10 to 50 percent in white and gray matter and returns to a first measured value.

* * * * *